United States Patent
Nolan et al.

[11] Patent Number: 6,128,820
[45] Date of Patent: Oct. 10, 2000

[54] METHOD OF REPAIRING DAMAGED TURBINE ROTOR WHEELS USING DIFFERENTIALLY CONTROLLED TEMPERATURES

[75] Inventors: John Francis Nolan, Latham; Gerald Richard Crawmer, Clifton Park; Eloy Vincent Emeterio, Amsterdam, all of N.Y.

[73] Assignee: General Electric Co., Schenectady, N.Y.

[21] Appl. No.: 09/200,725

[22] Filed: Nov. 27, 1998

Related U.S. Application Data

[60] Provisional application No. 60/104,961, Oct. 20, 1998.

[51] Int. Cl.$^7$ ..................................................... B23P 15/00
[52] U.S. Cl. .................... 29/889.1; 29/402.13; 29/402.16
[58] Field of Search ............................. 29/889.1, 402.08, 29/402.03, 402.07, 402.06, 402.13, 402.16

[56] References Cited

U.S. PATENT DOCUMENTS 5,575,145  11/1996  O'Neill et al. .......................... 29/889.1
5,755,031  5/1998  Baumgarten et al. ................. 29/889.1
5,765,993  11/1996  Weiss ..................................... 29/889.1

*Primary Examiner*—Irene Cuda
*Attorney, Agent, or Firm*—Nixon & Vanderhye

[57] ABSTRACT

A method of repairing a turbine rotor wheel having a damaged dovetail includes removing the damaged dovetail from the turbine wheel, leaving a turbine wheel body and welding a ring about the turbine wheel body in place of the removed damaged dovetail. During the welding process, including during preheating, welding or stress relieving, the temperature of the wheel body and ring is differentially controlled to introduce residual stresses in the ring. After welding a dovetail is formed in the ring for receiving turbine bucket dovetails. As a result, the ring has residual compressive stresses in a cold condition of the turbine whereby reduced net stresses in the ring in the location of the new dovetail during hot turbine operating conditions are reduced.

20 Claims, 10 Drawing Sheets

METHOD OF REPAIRING DAMAGED TURBINE ROTOR WHEELS USING DIFFERENTIALLY CONTROLLED TEMPERATURES

RELATED APPLICATIONS

This application is a continuation of provisional application Ser. No. 60/104,961, filed Oct. 20, 1998.

TECHNICAL FIELD

The present invention relates to the repair of turbine rotor wheel dovetails and particularly relates to repaired turbine rotor wheels and apparatus and methods for replacing a damaged rotor wheel dovetail with a forged replacement ring in which new dovetails are formed. The invention is particularly applicable to the repair of steam turbine rotors but is also applicable to gas turbine rotors.

BACKGROUND OF THE INVENTION

Steam turbines typically used for power generation are comprised of multiple stages, each having fixed partitions and a plurality of turbine buckets mounted on rotatable turbine wheels. The buckets are conventionally attached to the wheels by a dovetail connection. A number of different types of dovetails may be employed. For example, a finger-type dovetail is often used to secure the buckets and rotor wheel to one another. In that type of dovetail, the outer periphery of the rotor wheel has a plurality of axially spaced circumferentially extending stepped grooves for receiving complementary fingers on each of the bucket dovetails when the buckets are stacked about the rotor wheel. Pins are typically passed through registering openings of the dovetail fingers of each of the wheel and bucket dovetails to secure the buckets to the wheel. Another type of dovetail is a tangential entry dovetail. The turbine wheel and bucket dovetails have a generally complementary pine tree configuration. Also, in gas turbines, axial entry dovetails are sometimes employed. In any event, the dovetail connections between the buckets and wheels are highly stressed and, after years of operation, tend to wear out and crack. On low pressure steam turbine rotors, cracking occurs typically as a result of stress corrosion. In high pressure steam turbine rotors, cracking typically occurs as a result of creep rupture and/or low cycle fatigue. It will be appreciated that the magnitude of the stresses in the rotor wheel are very substantial at the radial location of the wheel dovetail because of stress concentration factors developed by the dovetail geometry. That is, peak stresses are significantly higher in the wheel dovetail as compared with locations radially inwardly which have significantly lower stresses. For example, the pin openings in the finger-type dovetail, and the machined areas of the wheel defining the fingers concentrate the stresses in the dovetail area and, over time, cause cracking as a result of one or more of the aforementioned failure mechanisms.

Because of the mass and the rotational speed of a turbine, e.g., typically on the order of 3600 rpm, significant damage to the turbine, its housing and surrounds, as well as injury to turbine operators, can occur should cracks develop in the wheel dovetail sufficiently to permit one or more of the buckets to fly off the rotor wheel. Prior to the present invention, the utility operator, upon inspection of the rotor and identification of a significant crack in one or more of the turbine wheels, particularly at the dovetail connections, had essentially two choices: first, the entire rotor could be replaced and, secondly, the damaged rotor wheel could be repaired by employing a conventional weld buildup process. The first option is costly and may involve considerable costly downtime before a new rotor is available for installation. For that reason, removal of the damaged dovetail from the rotor wheel and replacement of the removed dovetail with built-up weld material has been the principal choice as the method of repairing damaged turbine wheels.

In a typical weld buildup process, the rotor is first removed from the turbine and the buckets are removed from the turbine wheel. The damaged dovetail is then removed from the wheel and weld material is applied to the rim of the wheel in multiple passes to provide a weld build up which can later be machined to provide the dovetail. The weld material can be the same as or different from the material from which the rotor wheel is made. For example, in U.S. Pat. No. 4,940,390, a TIG welding process is used to deposit a weld metal of 12 Cr material onto Ni—Cr—Mo—V. 12 Cr material is much more resistant to stress corrosion cracking than Ni—Cr—Mo—V. However, welding processes in general are prone to defects such as porosity and slag inclusions in the weld metal and it is difficult to optimize the properties of the weld material when it is being deposited on the wheel.

There are, however, specific limitations on the buildup of weld material on a wheel which render turbine rotor wheel buildups as a method of repair only marginally satisfactory. On one hand, the weld buildup material desirably should be as resistant and as strong as possible to resist stress corrosion cracking in service. On the other hand, the weld material must be weldable to the base material, i.e., the forging of the rotor. To provide such weldable material, carbon and certain other elements must be kept relatively low to render the material weldable. This results in a dovetail lower in strength as compared with what could be achieved by supplying a replacement rotor forging. Therefore weld buildups inherently limit the capability to provide optimum material for resistance to stress corrosion cracking, creep rupture and cycle fatigue. The resulting weld buildup typically sacrifices tensile and yield strength to accommodate the need for a material weldable to the base material. This lower strength, together with the tendency for weld defects to grow during operation of the turbine, can limit the life expectancy of the repair to well below that of a replacement rotor forging.

Stress relief is also an important consideration in employing weld buildups for rotor wheel repair. Typically, the weld buildup is applied to the rotor, while the rotor axis lies in a horizontal position. However, to stress-relieve the rotor by application of heat, conventional methodology provides for hanging the rotor vertically, i.e., the rotor axis lies vertically. It was believed that the application of heat for stress relief purposes must be applied while the rotor is vertical to achieve uniformity of applied heat and uniform stress relief about the rotor. This involves substantial handling of the rotor with attendant risk of damage to the rotor.

Accordingly, there has developed a need for a repaired turbine rotor wheel dovetail wherein the material of the dovetails has the same as or increased resistance to failure mechanisms, such as stress corrosion cracking, creep rupture and cycle fatigue, as well as improved methods for repairing the dovetails of turbine rotor wheels.

BRIEF SUMMARY OF THE INVENTION

In accordance with one aspect of the present invention, there is provided a dovetail repair for a turbine rotor which, instead of a weld buildup repair, provides a ring replacement, typically a forging, for the entirety of the damaged dovetail and which forged ring can be formed of the same or improved materials in comparison with a replacement rotor material wherein the same or improved resistance to the various failure mechanisms is obtained. The replacement ring, forged or cast, is beneficially virtually free of defects and which defects might otherwise be extant in repaired dovetail characterized by a weld buildup of the same or similar material. Also, the material of the replacement ring is not a function of the welding process or the weld material employed to secure the ring to the rim of the wheel body after the damaged dovetail has been removed. Consequently, the forged replacement ring can be formed of materials which provide optimum properties for resistance to one or more of the different types of failure mechanisms. For example, for rotors formed of Ni—Cr—Mo—V or Cr—Mo—V or 12 Cr, a 12 Cr material such as 12% CrCb or an Inconel-based material can be employed. The weld material can be any weld material which is compatible with both the base material and the forged ring material, for example, a 12 Cr—Ni—Mo. The nature of the weld material is less significant to the welding process employed in this invention because the weld is formed along a relatively low stress area of the wheel and the only purpose of the weld is to join the wheel and the ring. That is, the weld material is not required to be as resistant to high stresses as is the dovetail per se.

The substantially defect-free replacement forged ring can be welded to the rim of the wheel body by a fine-line welding technique. Characteristic of the fine-line welding technique is the provision of a substantially linearly extending non-beveled extremely narrow groove which does not introduce significant porosity or slag into the weld material and which is relatively unsusceptible to welding problems when welding on materials usually considered difficult to weld on. By using the fine-line welding technique and locating the weld in a low stress region of the wheel, the forging can be formed of the most optimal material and the material can be selected to increase the strength and damage-resistant properties, e.g., by using forgings of relatively high carbon, columbium and other favorable materials. Thus, forging material can be tailored to increase the resistance of the material to one or more of the anticipated failure mechanisms to a much higher degree than possible with a weld buildup.

Certain additional aspects of the present invention will become apparent upon an understanding of the process of repairing a damaged dovetail according to the present invention. Once it has been determined that the rotor is in need of repair, the rotor is lifted from the turbine and placed on a horizontal axis upon bearings enabling motorized rotation of the rotor, i.e., the damaged rotor is placed in a lathe. The buckets on the rotor wheel requiring a dovetail repair are removed, for example, by removing the pins of the finger-type dovetail, the buckets thereby being removable in a radial outward direction. The damaged dovetail is then removed from the wheel by a machine tool operation, leaving a wheel body having a reduced diameter rim. The annular cut through the wheel to remove the damaged dovetail is made at a relatively low stress location about the wheel, i.e., radially inwardly of the dovetail. Weld preps are provided on both the wheel rim and the I.D. of a replacement ring. The ring, of course, is previously fabricated of the desired material and sized for the wheel body on which it will form the dovetail replacement. The ring is preferably formed either in multiple sections, for example, two 180° sections or as a 360° ring and is applied about the rim of the rotor and temporarily secured, for example, by tack welding or bolting.

Induction coils are set up on a suitable jig for separately heating the replacement ring, the rotor wheel and rotor shaft. For example, a first set of induction coils are disposed about and in spaced relation to the outer diameter of the ring. A second set of induction coils are disposed in spaced relation to axial opposite side faces of the rotor wheel body. A third set of induction coils are disposed about the rotor shaft on opposite sides of the wheel body. The ring, wheel and rotor are thus selectively preheated to the same or different temperatures as desired for purposes noted below and as the rotor is rotating.

A welding head setup is also provided on one or both sides of the ring and wheel body. The setup includes a welding head having an electrode, e.g., a tungsten electrode, weld material in the form of a fine wire which can be constantly advanced into the weld area and an inert gas delivery system. The electrode, weld wire and tubes are inserted in a generally axial direction in the axial opening between the ring and wheel rim. Also mounted on the welding jig are a pair of cameras for viewing the leading and trailing portions of the weld as the weld progresses. Thus, with the rotor rotating, an arc is struck and weld material is deposited, initially along the interior of the groove, i.e., along the weld prep. The weld may be single or double-sided. In a double-sided weld prep, after two or three passes, weld material is similarly provided along the interior of the groove opening along the opposite side of the wheel by the same or an additional welding head setup. After these initial passes, the multiple passes of the weld material may be provided in one or both grooves as the rotor rotates, the welding head being withdrawn in opposite axial directions in accordance with the thickness of the weld material applied during each pass. With the induction heating continuing during the welding process, the weld is completed by completely filling the annular grooves on opposite sides of the wheels with weld material.

As the weld passes are made, the welds can be inspected to ensure optimum weld quality. To accomplish this, cameras with high-powered lenses are used both on the leading and trailing sides of the weld to provide constant visual inspection. Additionally, an ultrasonic transducer is applied to the outer ring so that any defects too small to be seen visually in the welding can be ultrasonically detected before additional weld material is deposited in the groove in subsequent passes. The ultrasonic transducer is jacketed in a manifold having a cooling medium inlet and outlet whereby the transducer can be maintained at a cool temperature in the welding environment. In the event a defect is identified, the weld head setup can be displaced away from the wheel and the machining tool used to cut away one or more of the weld material deposits, including the defective weld.

Once the welding is complete, and in the case of a segmented ring, the ends of the ring sections are butt-welded to one another. To accomplish this, runoff blocks are welded to opposite sides of the ring and wheel body. The blocks have slots which are aligned with the groove of the butt-weld joint. The same or a similar type welding apparatus is mounted on a track, in turn mounted on a frame coupled to the ring. By traversing the welding apparatus back and forth along the track and depositing weld material in the butt-weld groove and runoff block slots, the weld material is built up in the groove. Upon completion of the butt-weld, the blocks are cut from the ring and the butt-welding head is removed.

A stress relief is then performed while the rotor lies on its horizontal axis. The induction coils continue to provide a heat treatment to the ring and rotor at selected elevated temperatures, thereby stress-relieving the weld. The rotor is then cooled down at a controlled rate by controlling the heat applied to the rotor by the induction coils. A final ultrasonic inspection of the cold rotor is then effected. Assuming the welds are without defect, the cutting machine is next employed to form the dovetails in the forged ring now welded to the rotor wheel body. In a finger-type dovetail, a milling head is secured to the machine and cuts the fingers in the outer surface of the ring. After forming the dovetail, the annular welds are typically shot-peened to introduce compressive stresses along the outer surfaces of the annular welds. These compressive stresses increase the resistance of the material to stress corrosion cracking. Subsequent to shot-peening, the rotor is balanced and the buckets are disposed in the new dovetail. The repaired rotor is then placed back in service in the turbine.

Having described the method of repair in general terms, it will be appreciated that there are a number of significant aspects of this repair and the repair process. For example, using separate heating zones on both the ring and rotor permits the same or different temperatures to be applied to the ring and wheel body during preheat, welding and stress relief by the induction coils to introduce and control residual stresses in the rotor. From the standpoint of controlling, reducing or eliminating the likelihood of failure from stress corrosion, rupture or fatigue or other failure mechanisms, it is desirable to have either low or no tensile stresses or to provide residual compressive stresses in the wheel dovetail. If the area of concern, i.e., the dovetail, has residual compressive stresses when the turbine is cold, those compressive stresses, when coupled with the tensile stresses during turbine operation are additive. The net result is a lower overall tensile stress during operation in the area of concern, i.e., the dovetail. To accomplish this, the ring and wheel body can be differentially heated during preheating, welding and stress relief to control the temperature of the ring and wheel body separately and thereby produce desired residual stresses. While in general, stress relief is used to desirably eliminate residual stresses, the present process enables the introduction of residual stress selectively by controlling the temperature of the ring and wheel body separately during the welding process by the multiple induction heating system and by providing a replacement ring (in contrast to a weld buildup in which it is impossible to control the weld metal at a different temperature than the wheel during welding). Accordingly, the temperatures of the rings, wheel body and shaft are monitored during preheating, welding and stress relief as the rotor is continuously spun during those processes. To accomplish that, thermocouples are applied to the ring and rotor. The thermocouples employ radio transmitters to transmit a temperature indicative signal to a controller which, in turn, controls the power applied to the induction machines thereby controlling the heat applied to the ring, wheel body and shaft. For example, the I.D. and O.D. of the replacement ring and the wheel rim may be machined to different sizes. Alternatively, during preheat, the ring may be brought up to a higher temperature than the wheel body so that the ring expands. With the ring overlying the wheel body, its temperature may be lowered to contract the ring and shrink it about the wheel body. While controlling the temperature of the wheel body and ring separately, the narrow groove welding goes forward and has a weld heat input which has a negligible effect on ring and rim temperature and hence distortion. During stress relief, the temperatures of the wheel body and ring are elevated to eliminate and temper residual stresses in the heat-affected zone of the weld. That is, the thermocouple sensing devices, in conjunction with the separately controlled induction heating arrangement, control and isolate the stress relief temperature to a relatively small confined area such that residual stresses in the ring and wheel body are not eliminated and are controlled to desirable magnitudes. Thus, the ring and rim temperatures are separately controlled during fit-up, preheat, welding, stress relief and cooling. When cooled, residual stresses result in the ring and rim. In this manner, compressive stresses are introduced in the ring in the cold condition of the turbine. With such controlled compressive stresses, the tensile stresses encountered during turbine operation are offset and the result is a lower residual stress in the turbine wheel dovetail.

As a specific example of the manner of introducing residual compressive stresses in the dovetail of the replacement rotor wheel, the material of the ring may be selected such that its coefficient of thermal expansion is different, e.g., less than the material of the rotor wheel body after the damaged dovetail has been removed. That is, a replacement ring, for example, formed of 12 CrCb will expand less in response to increased temperature than the Ni—Cr—Mo—V material of the rotor. With the new ring formed to have an I.D. slightly greater than the O.D. of the rotor wheel rim to define the narrow groove for welding purposes, the welding process goes forward as previously described. During stress-relief, the temperature of the replacement ring and rotor wheel after welding is raised, e.g., to approximately 1100–1150° F. Alternatively, temperatures of the ring and rotor wheel body during stress relief can be raised to different temperatures, e.g., the temperature of the rotor wheel body is elevated above the temperature of the ring by controlling the power supplied the induction coils. In either case, the rotor wheel body tends to expand radially outwardly to a greater extent than the replacement ring. As a consequence, the rotor wheel body is placed in compression and the ring in tension. During the period of stress-relief, for example, when holding the temperature(s) for a period of time on the order of 15 to 20 hours, both materials yield and the stresses are reduced or eliminated. Upon cooling, however, and because the wheel body tends to contract to a greater extent than the ring, the ring is placed under compression and the wheel body in tension. Thus, residual compressive stresses are desirably introduced into the dovetail of the replacement wheel.

It will be appreciated that the rotor wheel body and ring may be formed of materials having the same coefficients of thermal expansion. In that case, the different residual stresses are introduced by applying different temperatures to the wheel body and ring during stress relief. It will also be appreciated that the residual stresses may be introduced by differentially controlling the temperatures of the ring and wheel body during welding whether the materials are the same or different and with or without stress relief. For example, Inconel does not require stress relief and by differentially controlling the temperatures of the ring and the wheel body during welding, residual stresses may be introduced. However, where stress relief is required, the temperatures or temperature must be controlled during such stress relief or otherwise residual stresses introduced, e.g., during welding, would be eliminated.

A further aspect of the present invention resides in the capacity to perform the dovetail repair from start to finish with the rotor in a horizontal position in the repair apparatus, i.e., the lathe. As noted previously, the weld buildup repairs of the prior art typically lift the rotor and place it in a vertical position for stress relief purposes. The rotor is then typically moved to yet another setup for machining. In the present invention, the rotor is set up on its horizontal axis in a lathe, and, while horizontal, the dovetail is machined from the damaged wheel, the remaining wheel body is weld-prepped, a replacement forging and wheel body are preheated and welded to one another, the wheel body and ring are stress-relieved, the repair is ultrasonically inspected, the rotor is finish-machined, and the weld is typically shot-peened. The rotor is continuously rotated to minimize distortion and the likelihood of a bowed rotor during the heating processes, including during preheat, welding and stress relief. The machine (repair station lathe) used to rotate the rotor is capable of being manually turned to prevent bowing in case of a power failure during stress relief. The steps of removal of buckets, removal of damaged dovetail, machining the wheel prep, installation of the replacement dovetail ring, stress relief, machining the dovetail in the ring, introducing compressive stresses into the weld, shot-peening, and balancing the rotor, if necessary, are all performed in the horizontal position of the rotor in a single repair station lathe. The present invention therefore eliminates the time and difficulty of manipulating the rotor such that the various processes can be performed on the rotor. It also greatly decreases the risk of damage to the rotor during handling and transportation. Consequently, it will be appreciated that all repair operations in accordance with the present invention are performed while the rotor lies in the repair apparatus, i.e., the repair station lathe. Additionally, the lathe itself is portable and therefore can be transported to the site of the repair which is considerably less costly than transporting the damaged rotor to a repair facility.

In a still further aspect of the present invention, a shielding system provided adjacent the weld head to ensure that the weld and weld puddle are continuously bathed in an inert gas, preferably a combination of argon and helium. While gas cups for shielding gas in TIG welding areas are commonly employed, the deep groove fine-line welding in the present invention renders it difficult to deliver and maintain shielding gas in the bottom of the groove. To solve this problem, one or more cover plates are provided adjacent the welding head on each axial face of the wheel body and ring to substantially overlie at least a portion of the annular weld groove. To enable welding using a fixed head while the rotor is rotating, the shield is carried by the frame carrying the stationary weld head. The shield comprises one or more cover plates which straddle the groove opening on opposite sides of the electrode to confine the gas in the groove or at least to minimize bleed of the gas from the welding site. The cover plate can be an arcuate section straddling the groove or a cover plate which extends and overlies up to the full 360° of the groove. Additionally, seals, for example, brush seals, may be interposed between the cover plate and the ring and wheel on opposite sides of the weld groove to seal off the area of the weld.

In a still further aspect of the present invention, ultrasonic examination of the welds during the application of the weld material in the groove is provided. It will be recalled that the preheat welding and stress relief processes are carried out while the rotor is in a hot state. Consequently, it is necessary to cool the ultrasonic transducer. To accomplish this, a conventional ultrasonic transducer is disposed in a manifold defined by an outer housing having seals at opposite ends of the housing such that a closed cooling cavity is formed between the manifold and transducer body. The manifold is provided with a cooling medium inlet and outlet. Consequently, the operator may apply the transducer to the surface of the ring while hot and inspect the weld while maintaining the transducer sufficiently cool to enable operation. By examining the weld as the weld is being formed in multiple passes along the annular grooves on opposite sides of the wheel body and ring, and in a hot condition of the rotor, any defects in the weld can be uncovered and eliminated prior to completion of the weld and without waiting for the rotor to cool.

In a preferred embodiment according to the present invention, there is provided a method of repairing a turbine rotor wheel having an annular damaged dovetail comprising the steps of removing the annular damaged dovetail from the turbine wheel leaving a reduced diameter turbine wheel body, welding a ring about the turbine wheel body in place of the removed damaged dovetail, differentially controlling the temperature of the wheel body and ring during welding and forming a dovetail in the ring for receiving turbine bucket dovetails.

In a further preferred embodiment according to the present invention, there is provided a method of repairing a turbine rotor wheel having an annular damaged dovetail comprising the steps of removing the damaged dovetail from a turbine wheel leaving a reduced diameter wheel body, welding a ring about the turbine wheel body in place of the damaged dovetail, controlling the temperature of the wheel body and ring to different temperatures while stress-relieving the wheel and ring and forming a dovetail in the ring for receiving turbine bucket dovetails.

In a still further preferred embodiment according to the present invention, there is provided a method of repairing a turbine rotor wheel having an annular damaged dovetail comprising the steps of removing the annular damaged dovetail from the turbine wheel leaving a reduced diameter turbine wheel body, welding a ring about the turbine wheel body in place of the removed damaged dovetail, introducing residual stresses in the ring and the wheel body different from one another and forming a dovetail in the ring for receiving turbine bucket dovetails.

Accordingly, it is primary object of the present invention to provide a novel and improved repaired turbine rotor wheel and/or processes for the repair of a damaged turbine rotor wheel.

DETAILED DESCRIPTION OF THE INVENTION

Figure 1:
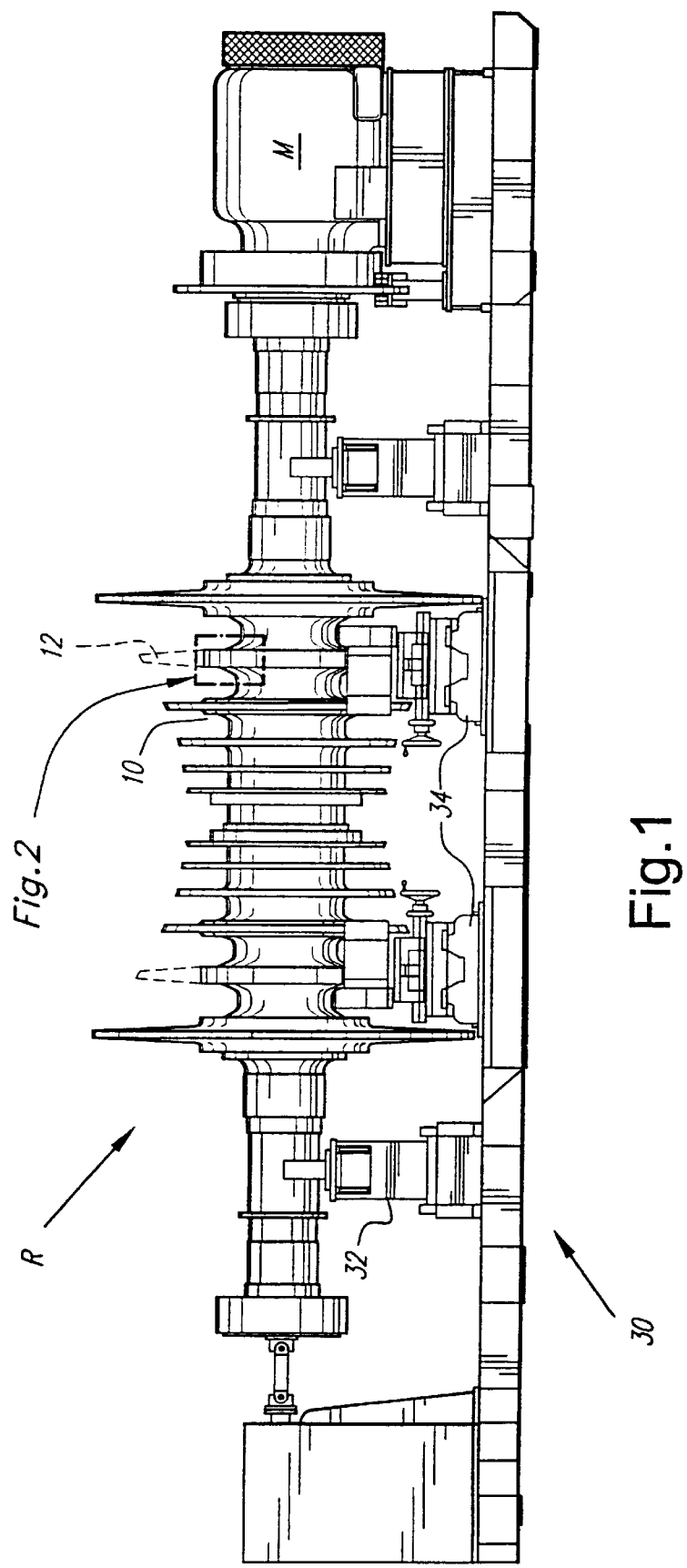
FIG. 1 is a side elevational view of an apparatus according to the present invention for use in repairing rotor wheel dovetails and illustrating a damaged rotor disposed in the apparatus.
Figure 2:
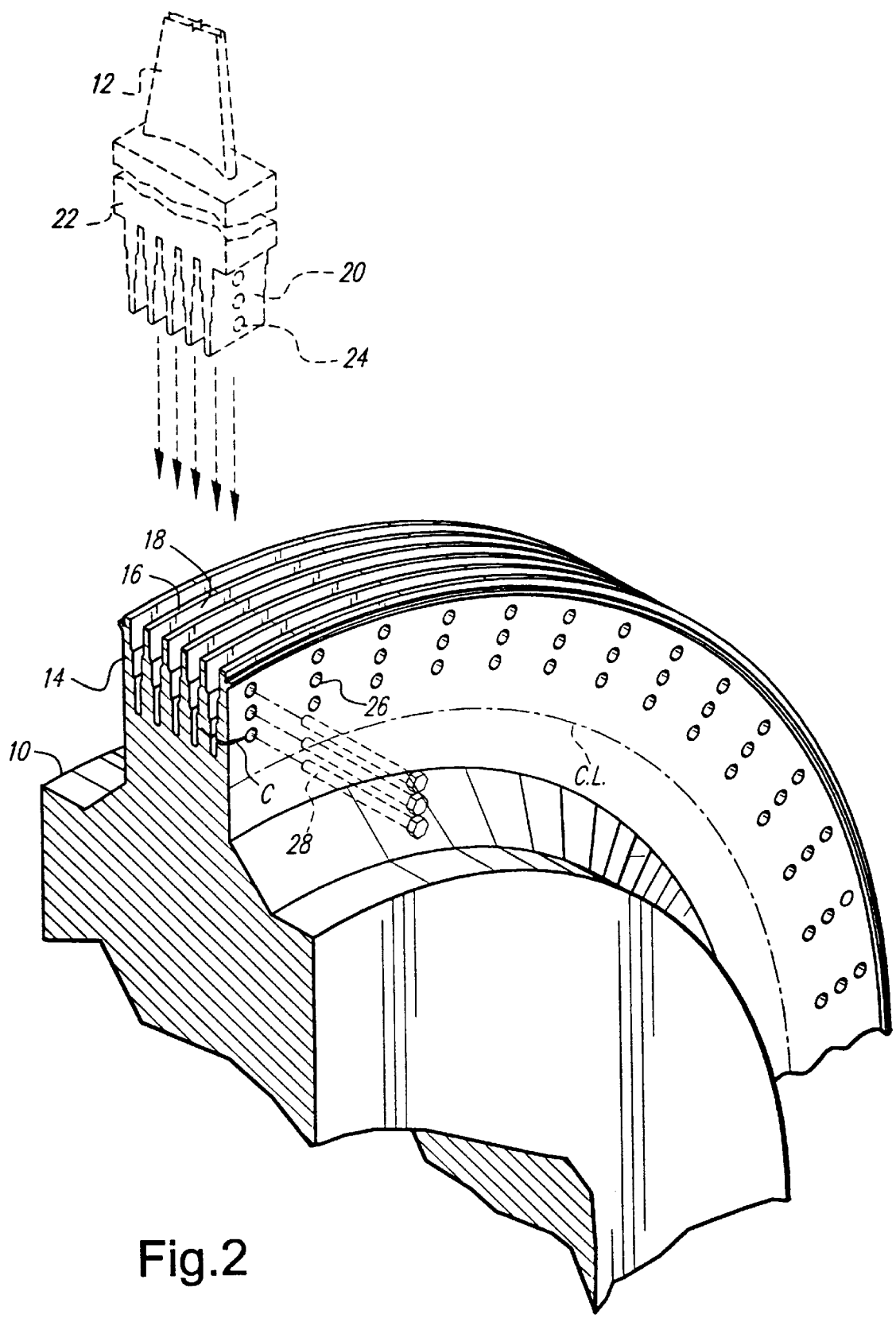
FIG. 2 is a fragmentary perspective view of a turbine rotor wheel illustrating a finger-type dovetail connection with turbine wheel buckets.

Referring now to the drawing Figures, particularly to FIGS. 1 and 2, there is illustrated a rotor, generally designated R, for a turbine, for example, a steam turbine, having a number of stages wherein each stage includes a rotor wheel 10 mounting a plurality of buckets 12. As best illustrated in FIG. 2, each rotor 10 includes a dovetail 14 comprised of a plurality of circumferentially extending, radially outwardly projecting fingers 16 defining grooves 18 therebetween. The grooves 18 receive complementary-shaped dovetail fingers 20 forming part of the bucket dovetail 22. As illustrated, the bucket dovetail 22 has a plurality, three being illustrated, of axially registering holes 24 through each finger 20 which, when the bucket dovetail is applied to the dovetail 14 of wheel 10, register with corresponding openings 26. Pins 28 are used to secure the buckets 12 to the wheel 10. It will be appreciated that the bucket dovetails are stacked against one another to form a circumferential array of buckets about the wheel and, in use, lie in the hot fluid path of the turbine, e.g., the steam path of a steam turbine.

Also illustrated in FIG. 2 is a crack C in dovetail 14 resulting from occurrence of one or more of the aforementioned failure mechanisms, for example, stress corrosion, creep rupture or cycle fatigue. Because the dovetail 14 lies in the high stress area of the wheel during use, failure invariably occurs in the dovetail 14 before any failure occurs in the remaining radially inward portions of the wheel 10. The present invention therefore involves the removal of the damaged dovetail 14 and its replacement by a forged ring which has or can be later machined to have a new dovetail for engagement by the bucket dovetails 22.

Referring back to FIG. 1, the rotor R is illustrated set up along its horizontal rotational axis in a lathe-type apparatus (repair station lathe), generally designated 30. The apparatus includes bearing supports 32 for the rotor, as well as a drive motor M for rotating the rotor R on the bearings 32. The structure 30 also includes a machining center 34, two such machining centers being illustrated, with each machining center having a head for interchangeably mounting a variety of tools, for example, a cutting tool and a milling head for use in the repair process, to be described. The apparatus 30 may be portable, i.e., the apparatus 30 can be transported to the site of the turbine and set up at that site to repair the turbine. Alternatively, of course, the apparatus 30 can be set up at a repair facility and the turbine rotors transported to that facility for repair.

Figure 3:
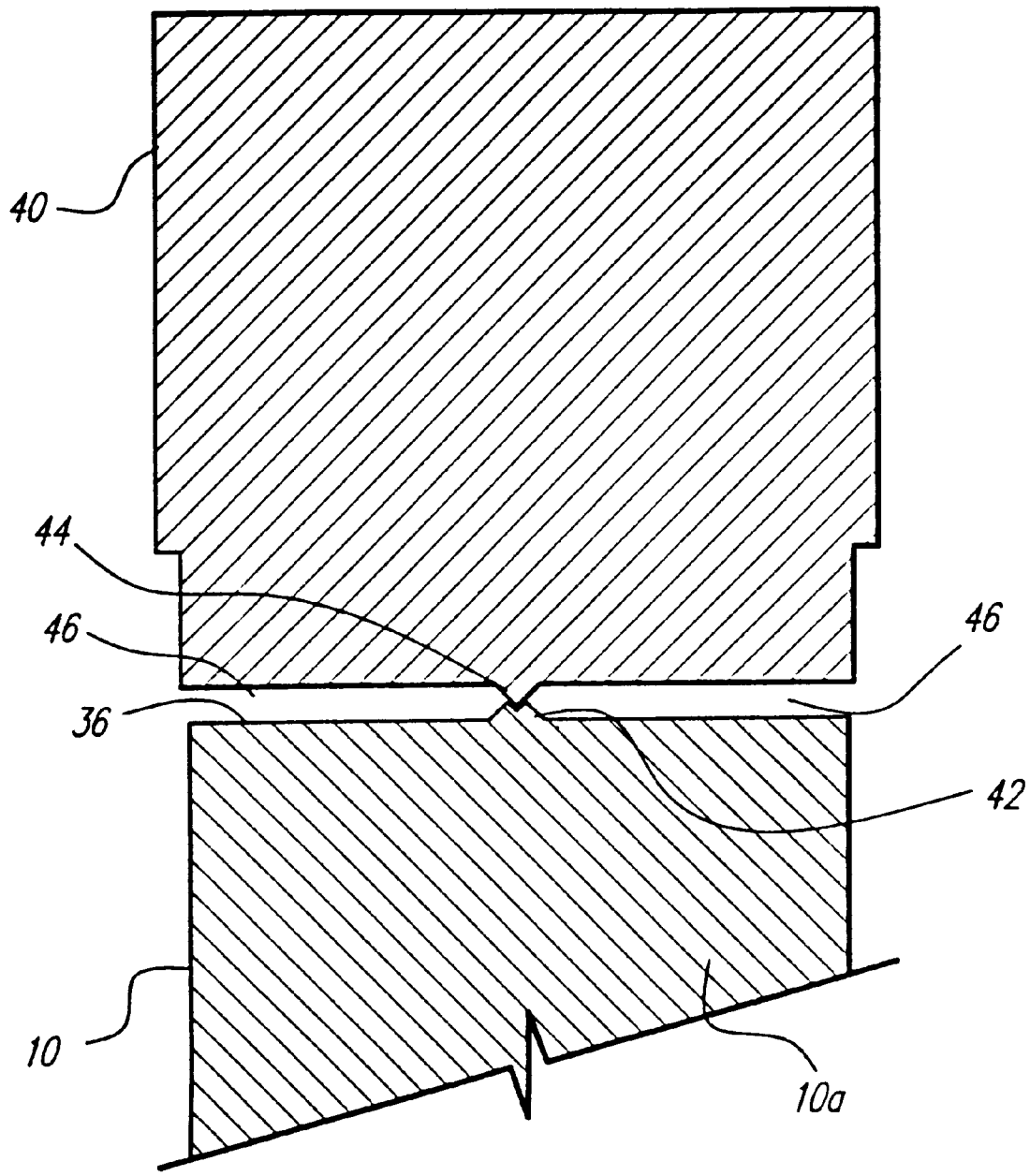
FIG. 3 is an enlarged fragmentary cross-sectional view illustrating a rim of a rotor wheel body after a damaged dovetail has been removed and a ring section applied to the wheel rim prior to welding.

While this description of the apparatus and method of the invention goes forward, describing the repair of a single wheel of the rotor R, it will be appreciated that with two or more machining centers 34 and other additional apparatus as detailed below, two or more of the wheels on a single rotor can be repaired simultaneously. The first part of the repair after mounting the rotor in apparatus 30 involves removal of the buckets 12. Next, the damaged dovetail 14 is removed. To accomplish this, a machining center 34 is set up with a cutting tool to remove or cut off the damaged dovetail 14, for example, along the cut line designated C.L. in FIG. 2. Consequently, the entire dovetail 14 about the wheel 10 is removed by continuously rotating the rotor past the cutting tool. The removal of the dovetail 14 leaves a wheel body 10$a$ having an outer rim 36 (FIG. 3). In accordance with one aspect of the present invention, a ring 40, preferably of forged material, is manufactured for fit about the rim 36. Ring 40 is provided in a single or in two or more arcuate ring sections, for example, two substantially 180° sections, although it will be appreciated that a complete circular forged or cast ring or more than two ring sections may be provided in certain circumstances. The material of the forged ring may be the same as or different from the material forming the rotor R and may be selected to have properties which increase its resistance to one or more of the failure mechanisms outlined above. For example, the rotor wheel may be formed of Ni—Cr—Mo—V or Cr—Mo—V, while the ring may be formed of 12% CrCb. The ring 40 is provided with or without dovetail grooves. If the ring is provided without grooves, they are later formed in the ring after the welding operation is completed.

As illustrated in FIG. 3, a weld prep is formed on each of the rim 36 and the I.D. of the ring 40. The weld prep may comprise, for example, a radial outward projection 42 formed on the outer rim 36 bearing a central V groove and a radial inward projection 44 formed along the I.D. of the ring 40. With those weld preps centrally located between opposite sides, i.e., axial faces of the ring and the wheel, it will be appreciated that a deep annular groove 46 is provided opening through each axially opposite face of the wheel and ring. The groove is a very narrow groove, on the order of 0.300 millimeters and may extend in an axial direction between the axial outer face and the weld prep a substantial distance, e.g., approximately one to twelve inches, dependent upon the wheel undergoing repair. As illustrated in FIG. 3, the grooves 46 are preferably not beveled, as is typical in a welding process.

Figure 4:
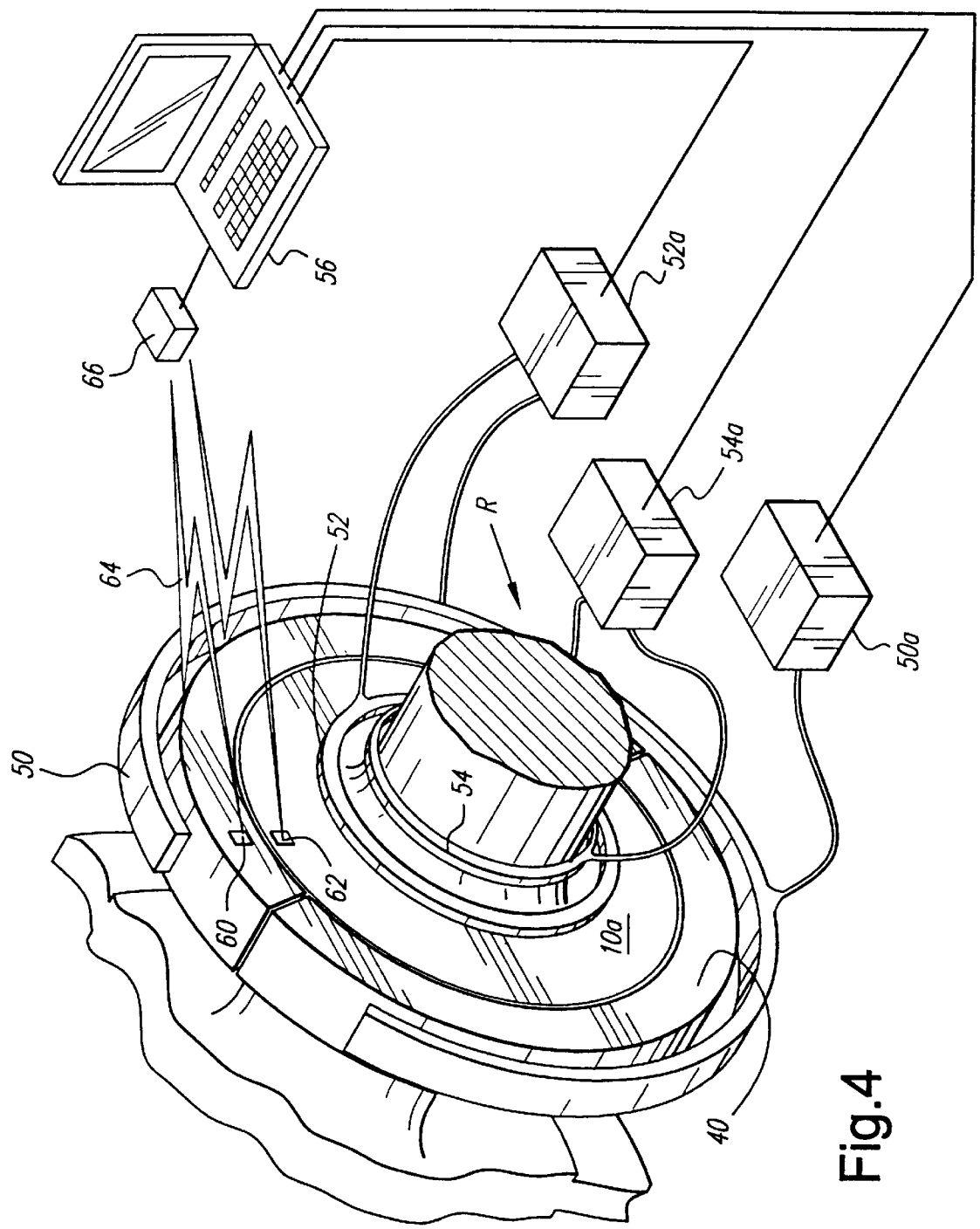
FIG. 4 is a fragmentary perspective view illustrating induction heating coils of induction machines for heating the rotor wheel body and ring and a control for the heating coils.

As illustrated in FIG. 4, the rotor R and particularly the wheel 10 and ring 40 are heated during the welding process by induction heating coils disposed about and spaced from the rotor. Particularly, at least one induction coil 50 is disposed about the rim of the ring 40 to heat the ring 40. A second induction coil 52 is spaced axially from and about the wheel body 10$a$ for heating the wheel. A third induction coil 54 is spaced about the shaft of the rotor. The coils 52 and 54 are located on each of the opposite sides of wheel 10. The coils are coupled to conventional induction heating machines 50$a$, 52$a$ and 54$a$ which, in turn, are controlled by a controller, e.g., a computer 56. It will be appreciated that by controlling the induction machines 50$a$, 52$a$ and 54$a$, the power supplied to the induction coils 50, 52 and 54, respectively, may be controlled to apply the same or different magnitudes of heat to the ring 40, wheel 10 and shaft of the rotor, respectively. In order to monitor the temperature of the ring 40, wheel 10 and shaft, thermocouples are appropriately applied, two thermocouples 60 and 62 being illustrated and applied about the ring and wheel body, respectively. While only one thermocouple is illustrated per ring and wheel body, it will be appreciated that a substantial number of thermocouples are provided about each of the ring 40, wheel body 10$a$ and shaft, for example, at different radial and circumferential positions thereof, to monitor the temperature of those elements. The thermocouples have radio transmitters which transmit a temperature indicative signal, illustrated by the jagged lines 64, to a receiver 66 which provides input to the controller 56. Consequently, the temperature of the ring, wheel body and shaft can be set to predetermined identical or different temperatures as desired and at different times during the repair process.

Figure 5:
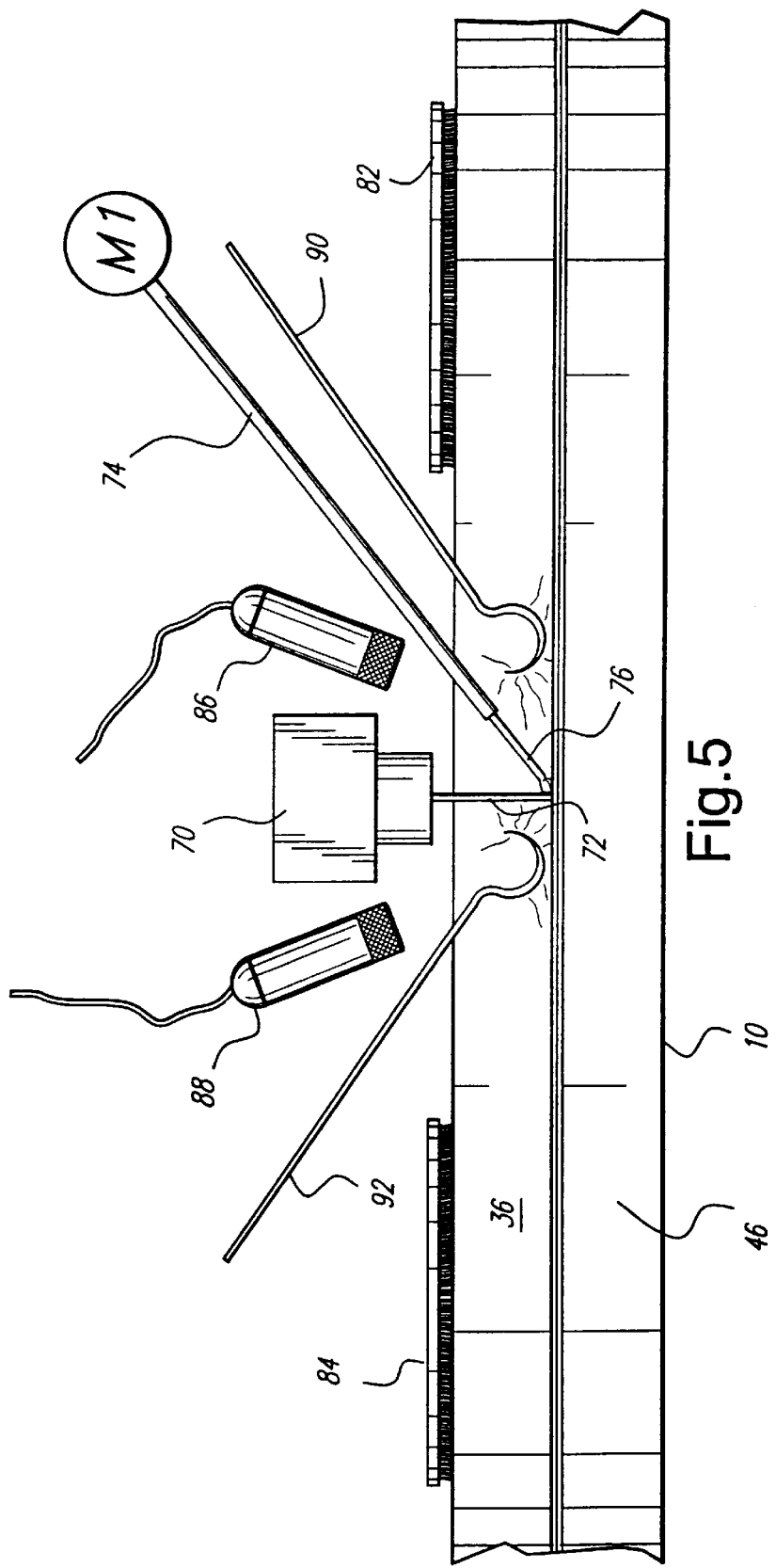
FIG. 5 is a fragmentary view looking radially inwardly along the groove between the rotor wheel body and ring and illustrating a weld setup on one side of the weld prep.
Figure 6:
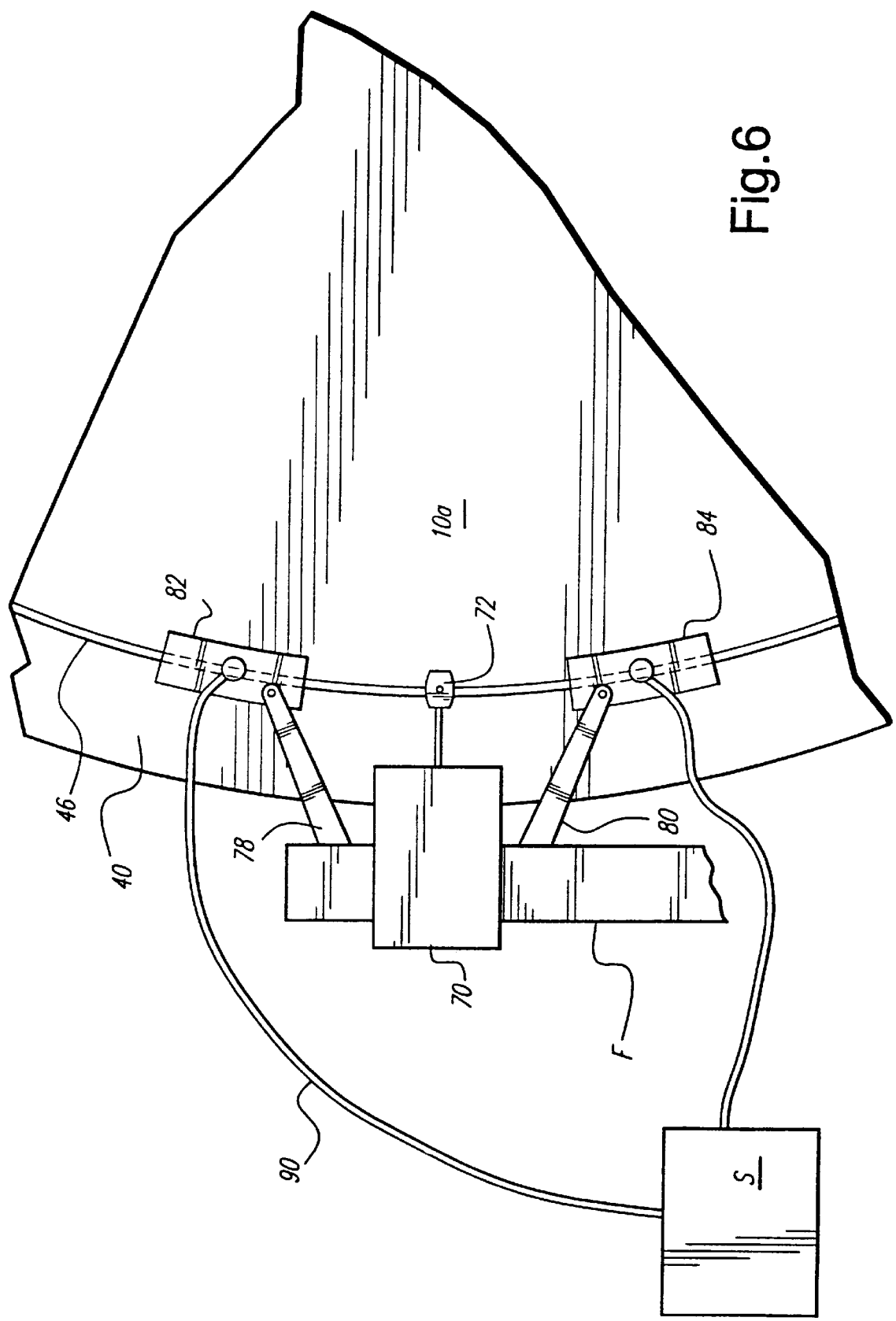
FIG. 6 is a fragmentary axial view schematically illustrating the welding apparatus applied to the groove between the rotor wheel body and ring.

Referring now to FIGS. 5 and 6, there is illustrated a welding setup for performing fine-line welding, i.e., welding the ring 40 and wheel body 10a one to the other. A suitable jig or frame F (FIG. 6) mounts a welding head body 70 which carries an electrode 72, preferably a tungsten electrode, for insertion into a groove 46 in an axial direction toward the weld prep 42 and 44. Also carried by the form F is a weld wire tube 74 carrying a weld wire 76 also mounted for insertion into the groove 46 in a generally axial direction. It will be appreciated that the weld wire may be advanced relative to the carrier tube 74 by a suitable electric motor M1 as is conventional and at a predetermined rate. Also mounted on the frame are a pair of upper and lower brackets 78 and 80, respectively, (FIG. 6) outer ends of which carry cover plates 82 and 84. The cover plates 82, 84 overlie the groove 46 opening through the axial face of the wheel body and ring, with the margins of the cover plates straddling the groove. The cover plates may extend a predetermined arcuate distance, for example, 25–30°, and lie spaced from one another leaving an opening therebetween for the tungsten electrode and a view port for cameras 86 and 88. Alternatively, the covers may extend completely about the annular groove, forming a single cover plate with openings therethrough for the tungsten electrode, view ports for cameras 86 and 88 and insert gas supply tubes 90 and 92. As illustrated in FIG. 5, the cameras are mounted on the frame F and are focused on the weld from both leading and trailing sides of the weld.

Figure 7:
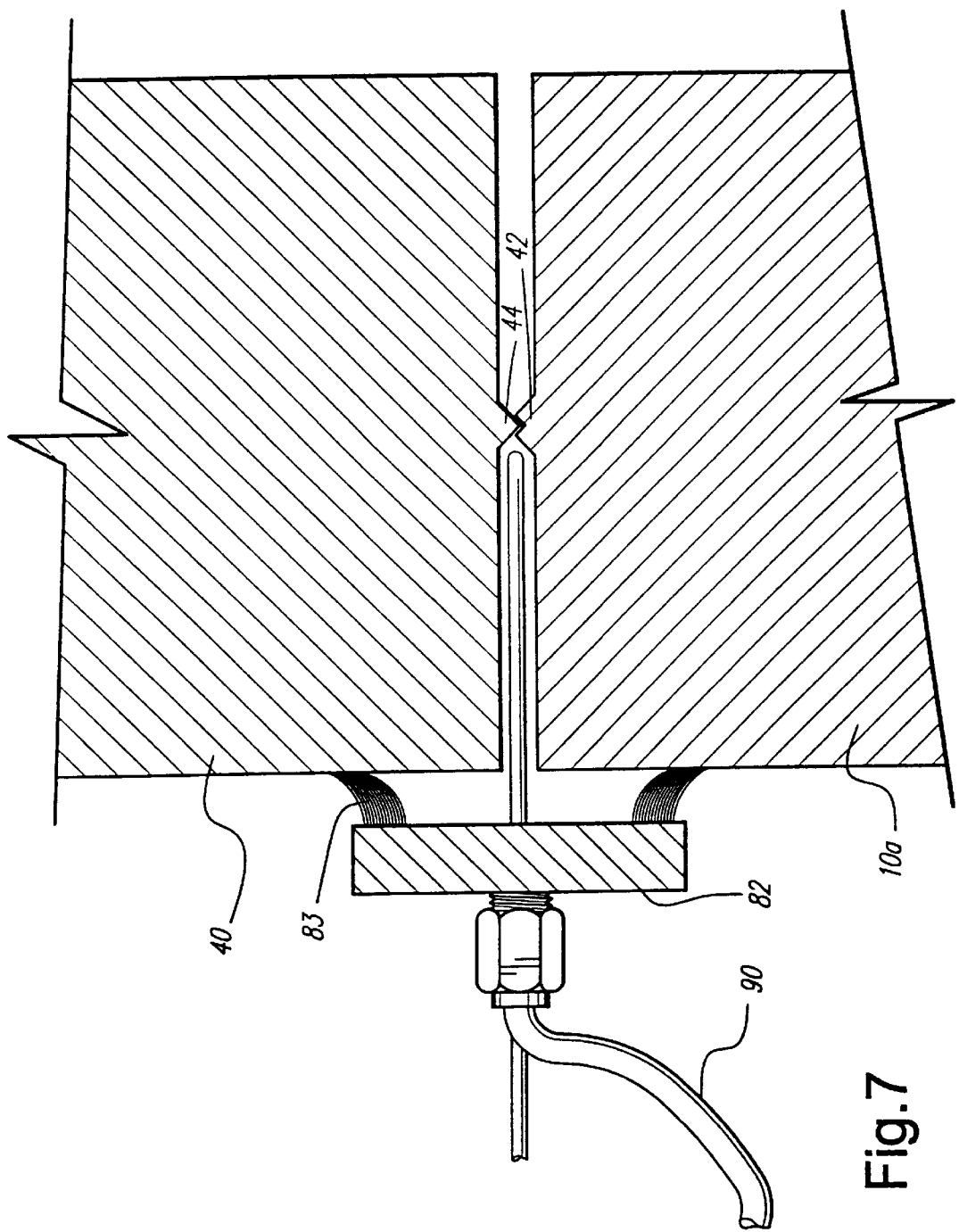
FIG. 7 is an enlarged fragmentary cross-sectional view of the groove illustrating the cover plate and seal.

An individual cover plate 82 or 84 is illustrated in FIG. 7, straddling the groove 46. In FIG. 7, optional seals are provided on opposite sides of the cover plate for engaging against the margins of the ring and wheel body. Additionally, inlet nipples may optionally be spaced periodically around the cover plates to provide additional inert gas inlets. For example, the seals may comprise brush seals 83. The purpose of the cover plates and optional seals are to confine or at least limit the outflow or bleed of welding gas supplied to the weld by the gas tubes 90 and 92. As illustrated in FIG. 5, the gas tubes 90 and 92 extend within the groove 46 and terminate in perforated hooked ends. Inert gas, preferably formed of a combination of argon and helium and supplied from a suitable source S, passes through tubes 90 and 92 and perforated end openings to full envelop the welding arc and applied weld material. The gas tubes 90 and 92 may, of course, extend through the cover plates 82 and 84.

It will be appreciated that as the rotor turns on the lathe 10, the tungsten electrode 72 strikes an arc with the base material, while the weld wire deposits weld material in the groove. Upon each pass of the rotor, the weld head body is displaced axially away from the groove to accommodate welding in the next pass until the groove is completely filled with weld material. It will also be appreciated that the same welding setup may be provided on both sides of the wheel undergoing repair such that the welds can be accomplished simultaneously from both sides of the wheel without distorting the wheel or ring.

Figure 11:
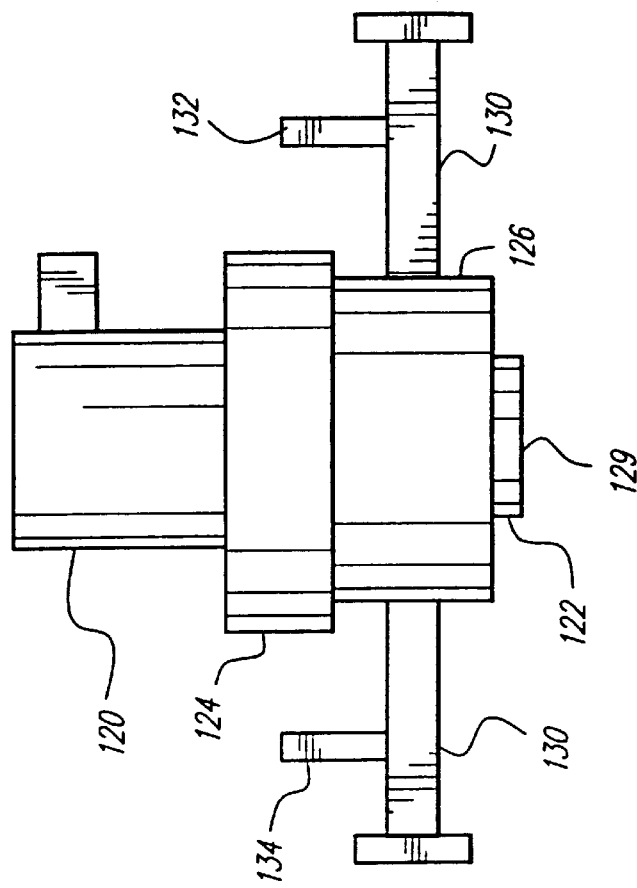
FIG. 11 is a side elevational view of the inspection equipment of FIG. 9.
Figure 10:
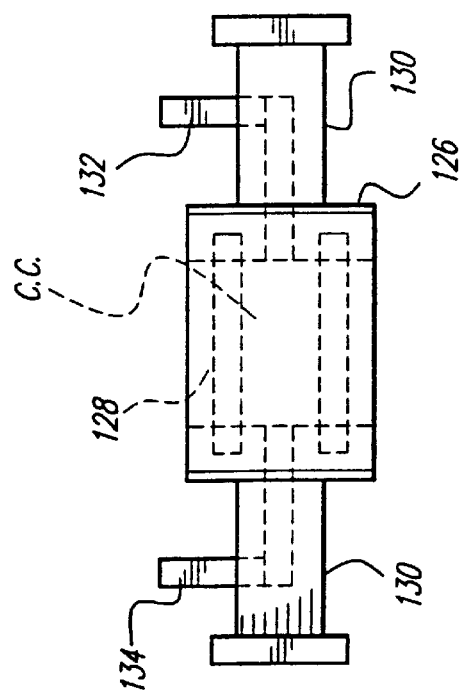
FIG. 10 is a side elevational view of an ultrasonic inspection device with cooling apparatus.

In the welding process, the welds are periodically inspected as the welds are being accomplished. For inspecting the annular welds securing the ring and wheel body to one another, an ultrasonic inspection device, illustrated in FIGS. 10 and 11, is provided. A standard ultrasonic transducer 120, for example, manufactured by, Model No., having a high temperature delay 122 is mounted in a mounting flange 124. The transducer 120, delay 122 and flange 124 are, in turn, mounted within a manifold 126. The manifold 126 includes a pair of seals, preferably O-ring seals 128, at opposite ends which seal against the housing of the transducer 120, defining with the transducer a cooling cavity C.C. within the manifold 126. A pair of ears 130 project from opposite sides of the manifold, providing handles for carrying the transducer. The handles include respective cooling medium inlet and outlet passages 132 and 134, respectively, for flowing a cooling medium through the cavity. For example, a cooling medium, such as water, may be supplied from a suitable supply for flow through the inlet 132 into the cooling cavity and out through the outlet 134 for return to the supply to maintain the temperature of the transducer 120 within allowed temperature limits. It will be appreciated that the transducer per se is conventional and includes an end 129 which transmits a signal through the high temperature delay 122 and into the ring 40 when the transducer is held against the outer surface of the ring. As the rotor turns, the ultrasonic signal is returned to the transducer and interpreted to determine the existence and location of any defects in the weld. By using the manifold, the use of a conventional transducer is permitted even at high temperature, permitting the results to be directly correlated with final U.T results in a cold condition.

Figure 8:
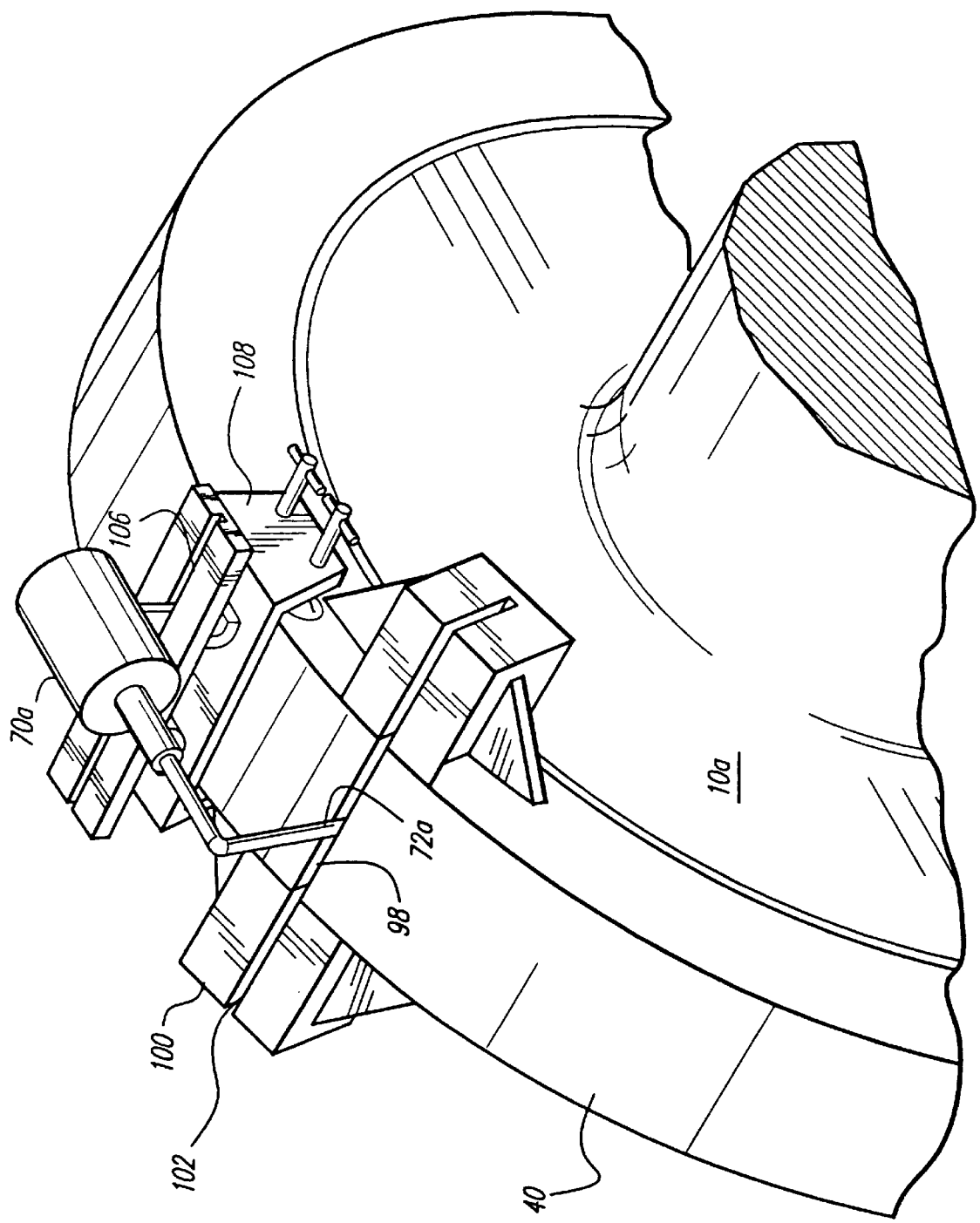
FIG. 8 is a fragmentary perspective view illustrating apparatus for forming butt-welds between forged ring sections.

Referring to FIG. 8, a similar type of weld head 70a may be provided for butt-welding the ends of the ring sections to one another. In order to butt-weld, however, a pair of runoff blocks 100 having slots 102 are secured on opposite sides of the ring and wheel with the slots 102 in registration with the groove 98 between the end faces of the ring sections. The runoff blocks 100 are welded and gussets are provided to reinforce the securement. The welding head is mounted on a track 106. The track 106, in turn, is mounted on a base 108 releasably secured to the ring 40 by suitable means, such as toggle bolts. The weld head 70a is mounted for longitudinal movement back and forth along the track 106. The weld head 70a also mounts a tungsten electrode 72a for disposition in the registering grooves 98 and 102. The head further mounts gas supply tubes, as well as weld wire material, not shown in these drawing Figures, for reception in the registering grooves and slots. By traversing the weld head back and forth along track 106, weld material may be supplied in multiple passes in the groove 98, building up the weld surface until it lies substantially flush with the O.D. of the ring. It will be appreciated that where two 180° ring sections are provided, the butt-welds are provided at diametrically opposite locations about the ring. Upon completion of the butt-weld, the welding head or heads are removed from the ring and the cutting tool of each machining center are employed to cut the runoff blocks from opposite sides of the ring.

Figure 9:
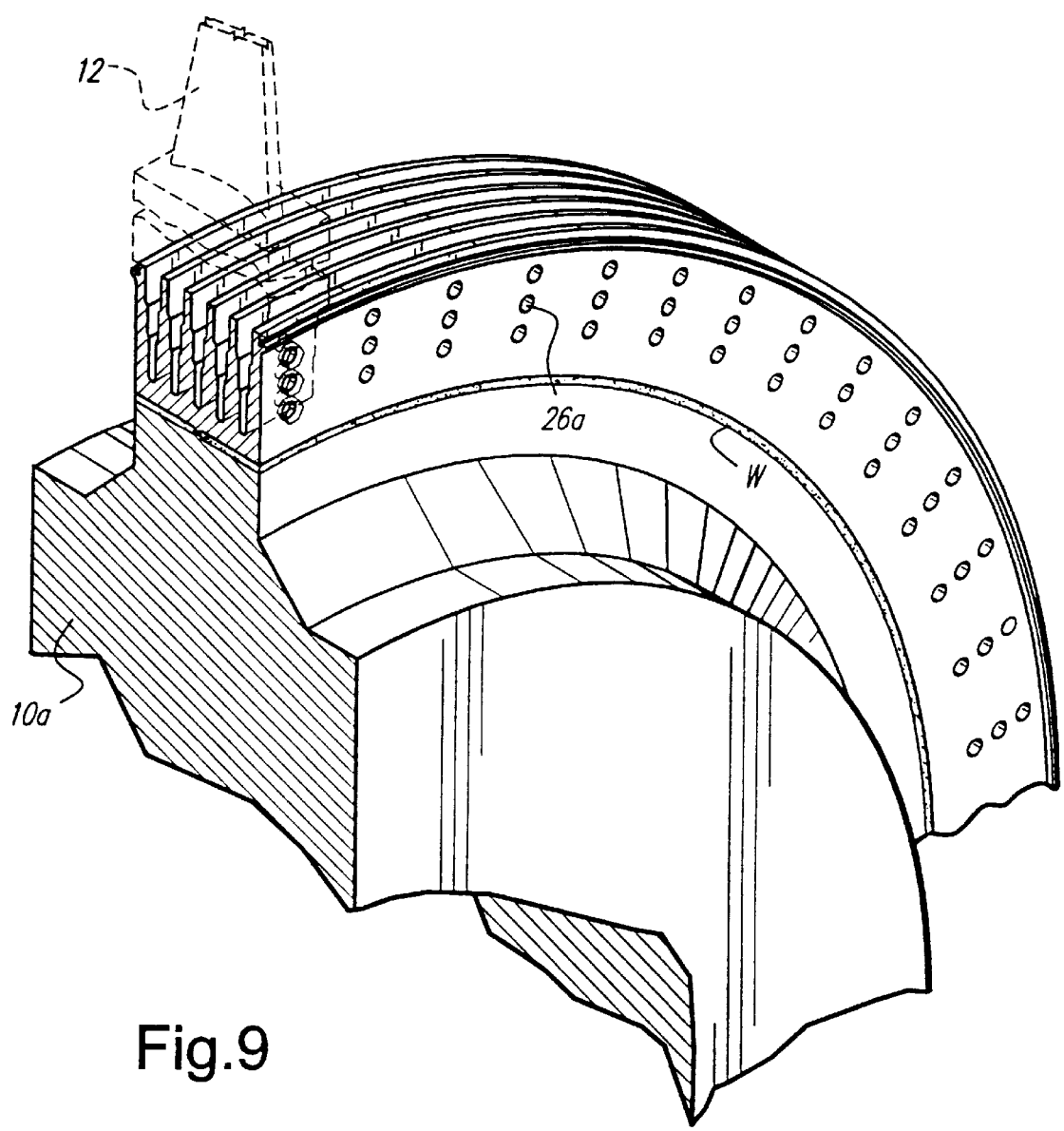
FIG. 9 is a view similar to FIG. 2 illustrating a repaired turbine rotor wheel.

After final inspection of the welds, the dovetails are formed in the ring 40. To accomplish this, the machining centers 34 are provided with milling heads for cutting the fingers in the outer rim of the ring as the rotor turns in the lathe. When the fingers are finally cut, into the ring, the pin holes 26a are formed to complete the dovetail of the repaired wheel illustrated in FIG. 9. Note also in FIG. 9 that the weld W lies at a location radially inwardly of the cut-in dovetail such that when the repaired rotor wheel is placed in service, the weld W lies at a low-stress area in the wheel.

In order to further prolong the life expectancy of the repaired rotor wheel, the weld W may be shot-peened. That is, small metal pellets are applied to the exposed surface of the welds on opposite sides of the repaired wheel to introduce compressive stresses in the exposed areas of the welds. As will be recalled, compressive stresses are highly resistant to stress corrosion cracking and, by shot-peening, compressive stresses are introduced on the weld surfaces. The pellets are introduced into the weld surface using high pressure compressed air at very high speeds to introduce compressive stresses on the outside surface of the weld. It will be appreciated that the inside surfaces of the weld are not exposed to the hot fluid, e.g., steam, in the steam path of a steam turbine. Finally, the rotor is balanced in the lathe. By spinning the rotor at a higher speed, the extent to which the rotor may be out of alignment can be determined. Balance weights can then be applied to the rotor to assure that the rotor is balanced for rotation about its long axis.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of repairing a turbine rotor wheel having an annular damaged dovetail comprising the steps of:

removing the annular damaged dovetail from the turbine wheel leaving a reduced diameter turbine wheel body;

welding a ring about the turbine wheel body in place of the removed damaged dovetail;

differentially controlling the temperature of the wheel body and ring during welding; and forming a dovetail in the ring for receiving turbine bucket dovetails.

2. A method according to claim 1 including monitoring the temperature of at least one of the wheel body and ring during welding and controlling the temperature of the one wheel body and ring in accordance with the monitored temperature to maintain the one wheel body and ring at a predetermined temperature.

3. A method according to claim 2 including rotating the wheel body and ring relative to a welding head during welding, transmitting the monitored temperature to a controller by radio transmission, and controlling the temperature of the wheel body and ring in accordance with the monitored temperature.

4. A method according to claim 1 including introducing residual stresses into at least one of said wheel body and said ring by differentially controlling the temperature of the wheel body and ring during welding.

5. A method according to claim 1 including differentially controlling the temperature of the wheel body and ring during preheating prior to welding.

6. A method according to claim 1 including differentially controlling the temperature of the wheel body and the ring while stress-relieving the wheel body and ring subsequent to welding the ring and wheel body to one another to introduce residual compressive stresses into the ring.

7. A method according to claim 1 including forming said wheel body and said ring with different materials.

8. A method according to claim 1 including heating the ring during welding to introduce compressive stresses in said ring in a cold condition of the turbine thereby reducing net stresses in the ring during hot turbine operating conditions.

9. A method of repairing a turbine rotor wheel having an annular damaged dovetail comprising the steps of:

removing the damaged dovetail from a turbine wheel leaving a reduced diameter wheel body;

welding a ring about the turbine wheel body in place of the damaged dovetail;

controlling the temperature of the wheel body and ring to different temperatures while stress-relieving the wheel and ring; and forming a dovetail in the ring for receiving turbine bucket dovetails.

10. A method according to claim 9 including introducing residual stresses into at least one of said wheel body and said ring by differentially controlling the temperature of the wheel body and ring during stress relief.

11. A method according to claim 9 including heating the ring during stress relief to introduce residual compressive stresses in said ring in a cold condition of the turbine thereby reducing net stresses in the ring during hot turbine operating conditions.

12. A method according to claim 9 including monitoring the temperature of at least one of the wheel body and ring during stress relief, transmitting the monitored temperature to a controller by radio transmission, and controlling the temperature of the wheel body and ring in accordance with the monitored temperature.

13. A method according to claim 9 including introducing residual compressive stresses into said ring during stress relief.

14. A method according to claim 9 including providing the ring and wheel body of materials with different coefficients of thermal expansion.

15. A method of repairing a turbine rotor wheel having an annular damaged dovetail comprising the steps of:

removing the annular damaged dovetail from the turbine wheel leaving a reduced diameter turbine wheel body;

welding a ring about the turbine wheel body in place of the removed damaged dovetail;

introducing residual stresses in said ring and said wheel body different from one another; and forming a dovetail in the ring for receiving turbine bucket dovetails.

16. A method according to claim 15 including differentially controlling the temperature of the wheel body and ring during welding to introduce compressive stresses in said ring.

17. A method according to claim 15 including stress-relieving the wheel body and ring subsequent to welding and differentially controlling the temperature of the wheel body and ring during stress relief to introduce compressive stresses in said ring.

18. A method according to claim 15 including providing the ring and wheel body of materials having substantially the same coefficient of thermal expansion, and differentially controlling the temperature of the ring and wheel body during the repair to introduce compressive stresses in said ring.

19. A method according to claim 15 including providing the ring and wheel body of materials having different coefficient of thermal expansion, and controlling the temperature of the ring and wheel body during the repair to introduce compressive stresses in said ring.

20. A method according to claim 19 including differentially controlling the temperature of the ring and wheel body during the repair to introduce compressive stresses in the ring.

* * * * *